Figure 1:
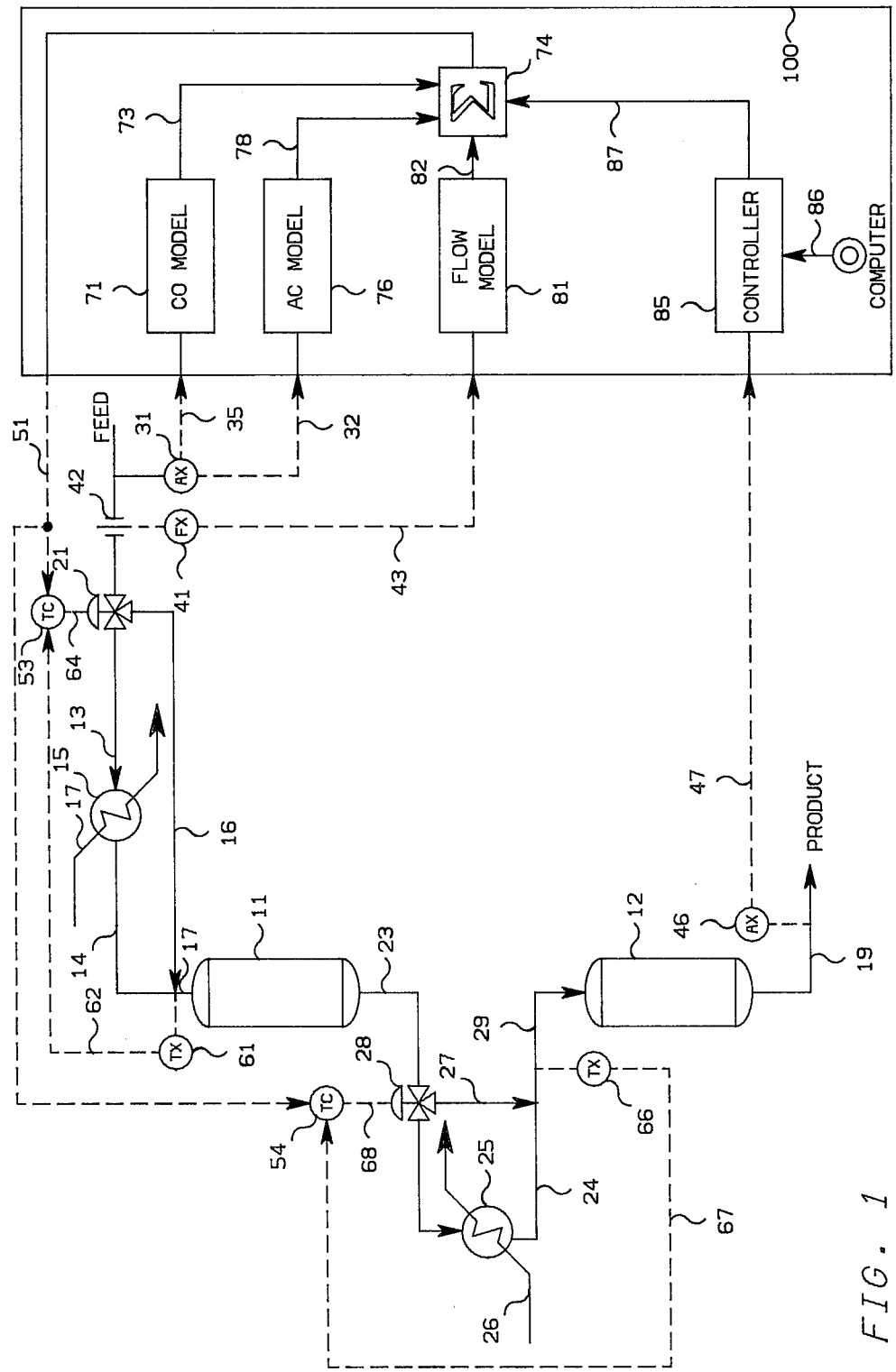

United States Patent [19]

Dibiano

[11] 4,367,354

[45] Jan. 4, 1983

[54] TEMPERATURE CONTROL OF A SELECTIVE HYDROGENATION PROCESS

[75] Inventor: Robert J. Dibiano, Sweeny, Tex.

[73] Assignee: Phillips Petroleum Company, Bartlesville, Okla.

[21] Appl. No.: 279,123

[22] Filed: Jun. 30, 1981

[51] Int. Cl.³ .......................... C07C 5/03; C07B 1/00
[52] U.S. Cl. .................................. 585/259; 260/690; 260/698; 260/700; 364/500; 364/557; 422/62; 585/263; 436/134; 436/142
[58] Field of Search ............................... 585/259, 263; 208/DIG. 1; 23/230 A; 422/62

[56] References Cited

U.S. PATENT DOCUMENTS 3,471,582 11/1967 Lupfer ................................. 260/677
3,656,911 4/1972 Hobbs ............................. 23/253 A
4,234,410 11/1980 Kelley .................................. 208/57
4,236,219 11/1980 Killebrew, Jr. et al. ........... 364/501
4,249,908 2/1981 Funk .................................. 23/230 A
4,251,674 2/1981 Callejos et al. ..................... 585/272

Primary Examiner—Delbert E. Gantz
Assistant Examiner—A. Pal

[57] ABSTRACT

In a selective hydrogenation process wherein at least two catalyst beds in series are utilized, the temperature of the feed stream flowing to the first catalyst bed and the temperature of the feed stream flowing from the first catalyst bed to the second catalyst bed are controlled using a combination of feed forward and feed back control. The feed forward control is based on the change in a process variable during a specified period of time. The feed back control is based on a comparison to the actual concentration of acetylene in the product stream flowing from the second catalyst bed to the desired concentration of acetylene in the product stream flowing from the second catalyst bed.

8 Claims, 1 Drawing Figure

TEMPERATURE CONTROL OF A SELECTIVE HYDROGENATION PROCESS

This invention relates to the temperature control of a process for the selective hydrogenation of acetylenic compounds in olefin-rich hydrocarbon streams. In one aspect, this invention relates to method and apparatus for accomplishing feed forward control of a process for the selective hydrogenation of acetylenic compounds in olefin-rich hydrocarbon streams.

In many exothermic chemical reactions it is necessary to control temperature within certain limits in order to maintain satisfactory yields and to prevent side reactions. This is particularly true in selective hydrogenation processes. For example, ethylene is commonly produced by the thermal cracking of hydrocarbon feedstocks. Unfortunately, some acetylene (impurity) is also produced which must be removed for many applications. This can be accomplished by selective catalytic hydrogenation of the acetylene.

In selective hydrogenation operations of this type, it is very important to maintain the operating temperature within narrow limits. If the temperature is too low, the hydrogenation reaction is not carried out in a sufficiently complete manner to remove the acetylene. If the temperature becomes too high, side reactions such as the hydrogenation of ethylene and the formation of polymers may result. It is also very important to prevent excessive temperatures from being reached because of the danger of explosions.

The desired concentration of acetylene in the product stream flowing from the selective hydrogenation process will generally be specified for any particular selective hydrogenation process. An analysis of the concentration of acetylene in the product stream is typically utilized to control the temperature of the selective hydrogenation process. The measured concentration is compared to a desired concentration with the results of the comparison being utilized to manipulate the temperature of the process in such a manner that the actual concentration of acetylene will be substantially equal to the desired concentration. This type of control is commonly referred to as feed back control.

If only feed back control is utilized, no change in the temperature of the process is made until a process change is reflected by a change in the acetylene concentration in the product stream. For example, carbon monoxide will generally be present in the feed to the selective hydrogenation process. Carbon monoxide tends to poison the hydrogenation catalyst. If the concentration of carbon monoxide in the feed changes, the temperature required for the hydrogenation of acetylene also changes. If the concentration of carbon monoxide in the feed changes and only feed back control is being utilized, the temperature of the process will not be changed as a function of the change in the concentration of carbon monoxide but will rather be changed only as a function of a change in the acetylene concentration in the product which is produced by the change in the concentration of carbon monoxide in the feed. This results in the actual concentration of acetylene deviating from the desired concentration of acetylene until such time as the change in the analysis of the product indicates that the temperature of the selective hydrogenation process should be changed. This may result in long periods of off-specification operation if process variables such as the concentration of carbon monoxide in the feed stream to the selective hydrogenation process are varying as a function of time.

Feed forward control, which is sometimes termed predictive control, provides a method by which closer control of a selective hydrogenation process can be obtained. In feed forward control, measurements of disturbances are used to provide a prediction of any resulting change in the process temperature which is necessary to compensate for any changes in the measured process variables so that on-specification operation can be maintained. Predictive or feed forward control provides a faster control response to changes in process variables. Actual measurements of the acetylene concentration of the product are utilized to correct the feed forward control signals as necessary.

It is thus an object of this invention to provide method and apparatus for accomplishing feed forward control of a process for the selective hydrogenation of acetylenic compounds in olefin-rich hydrocarbon streams.

In accordance with the present invention, a process for the selective hydrogenation of acetylenic compounds which utilizes two catalyst beds in series is feed forward controlled based on the change in a process variable during a specified period of time so as to maintain a desired reaction temperature in each catalyst bed. Two separate reactors may be utilized or a single reactor with two catalyst beds may be utilized so long as control of the temperature of the fluid stream flowing between the two catalyst beds is possible. Hereafter, the term first reactor and second reactor is utilized to describe the invention but the invention is not limited to the use of separate reactor vessels.

The feed forward control of the present invention is generally accomplished by analyzing the feed stream to the first reactor to provide an indication of the amount of carbon monoxide in the feed stream. This measurement is utilized to generate a feed forward control signal based on a nonlinear correlation which has been found between the concentration of carbon monoxide in the feed stream flowing to the first reactor and the temperature in the first and second reactors required to maintain a desired concentration of acetylene in the product stream flowing from the second reactor. The nonlinear correlation employs a change in the concentration of carbon monoxide in the feed stream in a specified period of time to relate concentration of carbon monoxide to the required temperature of the feed streams flowing to the first and second reactors. The thus generated feed forward control signal is biased by a feed back control signal which is based on an analysis of the concentration of acetylene in the product stream flowing from the second reactor.

Other process variables may also be utilized to generate feed forward control signals to the extent that there exists a correlation between the change of that process variable in a specified period of time and the amount that the temperature of the feed stream flowing to the first and second reactors must be changed to maintain a desired acetylene concentration in the product stream flowing from the second reactor when such process variables are changing. All feed forward control signals are generally summed with the feed back control signal to generate the final control signal which is utilized to manipulate the temperature of the feed streams flowing to the first and second reactors. In this manner, the required reaction temperatures are maintained in each reactor even when process variables are changing as a function of time.

Other objects and advantages of the invention will be apparent from the foregoing brief description of the invention and the appended claims as well as from the detailed description of the drawing which is briefly described as follows:

FIG. 1 is an illustration of a process for the selective hydrogenation of acetylenic compounds together with an associated control system for the process.

The invention is illustrated and described in terms of a specific selective hydrogenation process for the hydrogenation of acetylene in an ethylene product which also contains carbon monoxide. However, the applicability of the invention described herein extends to other process configurations such as using different heat exchanger configurations, more than two reactors or, as has been previously stated, two catalysts beds in a single reactor vessel. The applicability of the invention also extends to selective hydrogen of acetylene in other olefin-rich hydrocarbon streams such as propylene product streams or mixtures of ethylene and propylene where carbon monoxide is also present.

A specific control system configuration is set forth in FIG. 1 for the sake of illustration. However, the invention extends to different types of control system configurations which accomplish the purpose of the invention. Lines designated as signal lines in the drawings are electrical or pneumatic in this preferred embodiment. Generally, the signals provided from any transducer are electrical in form. However, the signals provided from flow sensors will generally be pneumatic in form. Transducing of these signals is not illustrated for the sake of simplicity because it is well known in the art that if a flow is measured in pneumatic form it must be transduced to electrical form if it is to be transmitted in electrical form by a flow transducer. Also, transducing of the signals from analog form to digital form or from digital form to analog form is not illustrated because such transducing is also well known in the art.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

A digital computer is used in the preferred embodiment of this invention to calculate the required control signals based on measured process parameters as well as set points supplied to the computer. Analog computers or other types of computing devices could also be used in the invention. The digital computer is preferably an OPTROL 7000 Process Computer System from Applied Automation, Inc., Bartlesville, Okla.

Signal lines are also utilized to represent the results of calculations carried out in a digital computer and the term "signal" is utilized to refer to such results. Thus, the term signal is used not only to refer to electrical currents or pneumatic pressures but is also used to refer to binary representations of a calculated or measured value.

Both the analog and digital controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable or a change in a desired factor or variable. An example of this is where a desired flow rate and an actual flow rate is compared by a controller. The output could be a signal representative of a desired change in the flow rate of some gas necessary to make the desired and actual flows equal. On the other hand, the same output signal could be scaled to represent a percentage or could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilizes a combination of pneumatic final control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

The terms "velocity" and "position" are commonly utilized in the art of process control to describe two different types of controllers or signals. A velocity controller is a controller which outputs a signal which is representative of a change required in a value such as the position of a device such as a control valve. A position controller is a controller which outputs a signal which is representative of a required value such as the position of a device such as a control valve. In like manner, a velocity signal is a signal which is representative of a change in a value while a position signal is representative of the actual value required. The present invention utilizes both position and velocity signals and controllers.

If the set point provided to a position controller is a velocity set point, the position controller will add the velocity set point to the position set point utilized one time period earlier to derive a new position set point which is then compared to the process variable provided to the position controller. Thus, a set point which is representative of a desired change will be converted to a set point that is representative of a desired value prior to being utilized by a position controller to manipulate the position of a device such as a control valve.

Referring now to FIG. 1, an ethylene feed stream containing some concentration of acetylene and carbon monoxide is introduced through conduit means 13 and 14 to the reactor 11 which contains a first catalyst bed containing a hydrogenation catalyst. Heat exchanger 15 is operably located between conduit means 13 and 14 such that fluid from conduit means 13 flows through heat exchanger 15. The heat exchanger 15 is utilized to provide heat to the feed stream flowing through conduit means 13 and 14 to the reactor 11. Steam or another suitable heating fluid is provided through conduit means 17 to the heat exchanger 15 and is utilized to provide heat to the feed flowing through conduit means 13 and 14. The control valve 21 is operably located in conduit means 13 and is utilized to split the flow of the feed between conduit means 13 and conduit means 16. The feed flowing through conduit means 14 and the bypass conduit means 16 are preferably mixed before the feed enters the reactor 11 through conduit means 17. The feed flowing through the bypass conduit means 16 is utilized as a quench fluid to provide further temperature control of the feed flowing to the reactor 11.

The effluent flowing from the reactor 11 is passed through conduit means 23 and 24 to the reactor 12 which contains a second catalyst bed containing a hydrogenation catalyst. Heat exchanger 25, which is operably located between conduit means 23 and 24, is utilized to provide a means for cooling the effluent flowing through conduit means 23 and 24. A cooling fluid, such as water, is provided through conduit means 26 to the heat exchanger 25. The control valve 28, which is operably located in conduit means 23, is utilized to control the relationship between the amount of effluent flowing from the reactor 11 which flows to the reactor 12 through the heat exchanger 25 and through the bypass conduit means 27. The effluent flowing through conduit means 27 may be considered the primary effluent stream and the effluent flowing through conduit means 23, the heat exchanger means 25, and conduit means 24 may be considered the quench fluid stream. The two fluid streams flowing through conduit means 27 and conduit means 24 are preferably mixed before entering the reactor 12 through conduit means 29.

The ethylene product, which will generally have a very low concentration of acetylene, is removed from the reactor 12 through conduit means 19. The product removed from the reactor 12 through conduit means 19 is generally provided to other portions of the ethylene manufacturing process.

The selective hydrogenation process described to this point is a conventional selective hydrogenation process. It is the manner in which the selective hydrogenation process is controlled which provides the novel features of the present invention.

Control of the selective hydrogenation process illustrated in FIG. 1 is generally accomplished by measuring a plurality of system parameters and supplying the measured parameters to computer means 100. In response to the measured inputs, computer means 100 calculates the change, if any, in the temperature of the feed stream flowing to the reactor 11 and the temperature of the feed stream flowing to the reactor 12 required to maintain a desired percent conversion of acetylene in the reactor 11 and to maintain the concentration of acetylene in the bottom product flowing from the reactor 12 through conduit means 19 at the predetermined level.

Analyzer transducer 31, which is in fluid communication with conduit means 13, provides a pair of output signals 32 and 35. Signal 32, which is representative of the concentration of acetylene in the feed stream flowing through conduit means 13, is provided from the analyzer transducer 31 to computer means 100. Signal 35, which is representative of the concentration of carbon monoxide in the feed stream flowing through conduit means 13, is also provided from the analyzer transducer 31 to computer means 100.

The flow transducer 41 in combination with the flow sensor 42, which is operably located in conduit means 13, provides an output signal 43 which is representative of the flow rate of the feed stream flowing through conduit means 13. Signal 43 is provided from the flow transducer 41 as an input to computer means 100.

Analyzer transducer 46, which is in fluid communication with conduit means 19, provides an output signal 47 which is representative of the concentration of acetylene in the product stream flowing through conduit means 19. Signal 47 is provided from the analyzer transducer 46 as an input to computer means 100.

In response to the described inputs, computer means 100 calculates a control signal 51 which is utilized in controlling the selective hydrogenation process illustrated in FIG. 1. Signal 51 is representative of the change required, if any, in the temperature of the feed stream flowing to the reactor 11 and the temperature of the feed stream flowing to the reactor 12 to compensate for changes in process variables. Signal 51 is provided from computer means 100 as an input to the temperature controller 53 and the temperature controller 54.

Both the temperature controller 53 and the temperature controller 54 are position controllers which are capable of accepting a velocity set point signal. As has previously been stated, the temperature controllers 53 and 54 are thus capable of storing a position set point signal. Initially, the position set point signals for the temperature controllers 53 and 54 are set to some desired values based on the experience of the process operators or based on the operating temperatures at which the process was operating when the switch to automatic control occurs. The position set point for the temperature controllers 53 and 54 is then changed periodically by signal 51 if changes are occurring in the process variables or if the actual concentration of acetylene in the product stream flowing through conduit means 18 is varying from the desired concentration. Thus, at time $t_0$, the position set point for the temperature controller 53 might be set at 150° F. while the position set point for the temperature controller 54 might be set at 158° F. At time $t_1$ the magnitude of signal 51 might be equal to $+1°$ F. Thus, at time $t_1$ the position set point for the temperature controller 53 would be 151° F. and the position set point for the temperature controller 54 would be 159° F. This process continues with the magnitude of signal 51 changing periodically. It is noted that if the process is at steady-state with no changes occurring in the process variables or in the concentration of the acetylene in the product stream flowing through conduit means 18, the magnitude of signal 51 will be essentially 0.

Any suitable period may be utilized for the updating of signal 51. The updating period is generally determined by the sample period for the analyzers 31 and 46. A typical period is about two and one-half minutes.

Temperature transducer 61 in combination with a temperature measuring device such as a thermocouple, which is operably located in conduit means 17, provides an output signal 62 which is representative of the temperature of the feed stream flowing through conduit means 17. Signal 62 is provided from the temperature transducer 61 as the process variable input to the temperature controller 53. The temperature controller 53 compares signal 62 to the position set point which has been generated in response to signal 51 for a particular time period and establishes an output signal 64 which is responsive to the difference between signal 62 and the position set point signal to which signal 62 was compared. Signal 64 is scaled so as to be representative of the position of the control valve 21 required to maintain the actual temperature of the feed stream flowing through conduit means 17 at a particular time substantially equal to the position set point for the temperature controller 53 at such particular time. Signal 64 is provided as a control signal from the temperature controller 53 to the control valve 21 and is utilized to manipulate the control valve 21.

Temperature transducer 66 in combination with a temperature measuring device such as a thermocouple which is operably located in conduit means 29, provides an output signal 67 which is representative of the temperature of the feed stream flowing through conduit means 29. Signal 67 is provided from the temperature transducer 66 as the process variable input to the temperature controller 54. The temperature controller 54 compares signal 67 to the position set point which has been generated in response to signal 51 for a particular time period and establishes an output signal 68 which is responsive to the difference between signal 67 and the position set point signal to which signal 67 was compared. Signal 68 is scaled so as to be representative of the position of the control valve 28 required to maintain the actual temperature of the feed stream flowing through conduit means 29 at a particular time substantially equal to the position set point for the temperature controller 54 at such particular time. Signal 68 is provided as a control signal from the temperature controller 54 to the control valve 28 and is utilized to manipulate the control valve 28.

The logic utilized to calculate the magnitude of the control signal 51 for each analysis period is as follows. As is illustrated in FIG. 1, signal 35, which is representative of the actual concentration of carbon monoxide in the feed stream flowing through conduit means 13, is provided to the carbon monoxide model 71. It has been found that the relationship between the carbon monoxide concentration in the feed and the change in the reaction temperature required to compensate for any changes in the concentration of carbon monoxide in the feed is given by Equation (1)

$$FF1 = (K_2 - CO_2)(K_1)((CO_2 - CO_1)/(t_2 - t_1)) \quad (1)$$

where
FF1 = feed forward control signal 73 provided by the CO model 71;
$CO_1$ = actual carbon monoxide concentration at a time $t_1$; $CO_2$ = actual carbon monoxide concentration at a time $t_2$; and
K1 and K2 are constants.

The magnitude of signal 73 is calculated in computer means 100 based on Equation (1) and the actual concentration of carbon monoxide in the feed stream. Signal 73 is provided from the CO model 71 as a first input to the summing block 74.

Signal 32, which is representative of the actual concentration of acetylene in the feed stream flowing through conduit means 13, is provided as an input to the acetylene model 76. The acetylene model 76 may be represented by Equation (2)

$$FF2 = ((AC_2 - AC_1)/(t_2 - t_1))(K_4) \quad (2)$$

where
FF2 = the magnitude of signal 78 which is provided as an output from the acetylene model 76;
$AC_1$ = actual concentration of acetylene at a time $t_1$;
$AC_2$ = actual concentration of acetylene at a time $t_2$; and
K4 is a constant.

Signal 78 is provided from the acetylene model 76 as a second input to the summing block 74.

Signal 43 which is representative of the flow rate of the feed stream is provided as an input to the flow model 81. The flow model 81 may be represented by Equation (3)

$$FF3 = ((F_2 - F_1)/(t_2 - t_1))(K_3) \quad (3)$$

where
FF3 = the magnitude of signal 82 which is provided as an output from the flow model 81;
$F_1$ = feed flow rate at a time $t_1$;
$F_2$ = feed flow rate at a time $t_2$; and
K3 is a constant.

Signal 82 is provided from the flow model 81 as a third input to the summing block 74.

Signal 47, which is representative of the actual concentration of acetylene in the product stream flowing through conduit means 19, is provided as an input to the controller block 85. The controller block 85 is also provided with a set point signal 86 which is representative of the desired concentration of acetylene in the product stream flowing through conduit means 19. In response to signals 47 and 86, the controller block 85 establishes an output signal 87 which is responsive to the difference between signals 47 and 86. Signal 87 is scaled so as to be representative of the change, if any, in the reaction temperatures required to maintain the actual concentration of acetylene substantially equal to the desired concentration of acetylene. Signal 87 is provided from the controller block 85 as a fourth input to the summing block 74.

Signals 73, 78 and 82 may be considered the feed forward terms of the control system of the present invention. Signal 87 may be considered the feed back term. Signals 73, 78, 82 and 87 are summed in the summing block 74 to establish signal 51.

It is noted that the feed forward control signal based on the carbon monoxide concentration is considered to be the only essential feed forward term for the control system of the present invention. The feed forward terms represented by signals 78 and 82 may be utilized if desired or may be completely nullified simply by setting the constants K3 and K4 equal to zero.

The magnitude of the constants K1–K4 may be determined by placing the acetylene hydrogenation process illustrated in FIG. 1 under feed back control only. The feed back control will change the process temperatures if the carbon monoxide concentration changes in the feed stream. The control system does not react as quickly as feed forward control based on the carbon monoxide concentration but data can be obtained indicating the temperature change which was required to maintain a desired acetylene concentration in the product stream in response to a particular change in the carbon monoxide concentration. Two sets of such data may be utilized to solve for K1 and K2 in Equation (1) since the remaining terms of Equation (1) will be known for each set of data. In like manner, constants K3 and K4 can be solved for based on observation of the process when the process is under feed back control only. Typical values of the constants K1–K4 are as follows:

K1 = 0.01
K2 = 5,000
K3 = 0.001
K4 = 0.001

The units for K1–K4 are such that signals 73, 78, 82 and 87 will have the units of temperature.

The control system illustrated in FIG. 1 provides both feed forward and feed back control of the temperature of the feed stream flowing to the reactor 11 and the temperature of the feed stream flowing to the reactor 12. Feed forward control is provided by the feed forward models which provide predictions of temperature changes needed to compensate for changes in either the concentration of acetylene or carbon monoxide in the feed stream flowing to reactor 11 or changes in the flow rate of the feed stream flowing to the reactor 11. Feed back control is provided by a comparison of the actual concentration of acetylene in the product stream flowing through conduit means 19 with the desired concentration of acetylene in the product stream flowing through conduit means 19. This combination of feed forward and feed back control allows close control of the acetylene concentration specification for the product stream and also allows close control of the temperatures of reactors 11 and 12 which avoids dangerous conditions.

The invention has been described in terms of a preferred embodiment as illustrated in FIG. 1. Specific components used in the practice of the invention as illustrated in FIG. 1 such as flow sensor 42; flow transducer 41; temperature transducers 61 and 66; temperature controllers 53 and 54; and pneumatic control valves 21 and 28 are each well known, commercially available control components such as are described at length in Perry's Chemical Engineers' Handbook, 4th Edition, Chapter 22, McGraw-Hill. The analyzer transducers 31 and 46 may be the 102 Process Chromatograph manufactured by Applied Automation, Inc.

For reasons of brevity, conventional auxiliary equipment commonly used in selective hydrogenation processes such as pumps, heat exchangers, additional measurement-control devices, etc., have not been included in the above description as they play no part in the explanation of the invention.

While the invention has been described in terms of the presently preferred embodiments, reasonable variations and modifications within the scope of the described invention and the appended claims are possible by those skilled in the art. Variations such as using an analog computer to perform the required calculations are within the scope of the invention. Other variations, such as having two catalyst beds in a single reactor, are within the scope of the invention as long as control can be exerted over the temperature of the feed stream flowing between the two catalyst beds.

That which is claimed is:

1. Apparatus comprising:
   a first catalyst bed;
   means for supplying an olefin-rich first feed stream containing acetylene and carbon monoxide to said first catalyst bed, a portion of said acetylene in said first feed stream being removed from said first feed stream in said first catalyst bed;
   a second catalyst bed;
   means for withdrawing the reaction effluent from said first catalyst bed as a first product stream and for supplying said first product stream as a second feed stream to said second catalyst bed, a portion of said acetylene in said second feed stream being removed from said second feed stream in said second catalyst bed;
   means for withdrawing the reaction effluent, containing a substantially reduced concentration of said acetylene, from said second catalyst bed as a second product stream;
   means for establishing a first signal representative of the concentration of carbon monoxide in said first feed stream at a time $t_1$;
   means for establishing a second signal representative of the concentration of carbon monoxide in said first feed stream at a time $t_2$ which is later in time than said time $t_1$;
   means for establishing a first feed forward control signal in response to said first and second signals, wherein said first feed forward control signal is a function of the concentration of carbon monoxide in said first feed stream at said time $t_2$ and a function of the change in the concentration of carbon monoxide in said first feed stream between said time $t_1$ and said time $t_2$ and wherein said first feed forward control signal is scaled so as to be representative of a change in the temperature of said first feed stream and said second feed stream required to maintain the actual acetylene concentration in said second product stream substantially equal to a desired acetylene concentration in said second product stream when the concentration of carbon monoxide changes between said time $t_1$ and said time $t_2$;
   means for establishing a third signal representative of the actual acetylene concentration in said second product stream at said time $t_2$;
   means for establishing a fourth signal representative of the desired acetylene concentration in said second product stream;
   means for comparing said third signal and said fourth signal and for establishing a feed back control signal which is responsive to the difference between said third signal and said fourth signal, wherein said feed back control signal is scaled so as to be representative of a temperature change required to maintain said third signal substantially equal to said fourth signal;

means for summing said first feed forward control signal and said feed back control signal to establish a temperature control signal; and means for manipulating the temperature of said first feed stream and the temperature of said second feed stream in response to said temperature control signal.

2. Apparatus in accordance with claim 1 additionally comprising:

means for establishing a fifth signal which is representative of the concentration of acetylene in said first feed stream at said time $t_1$;

means for establishing a sixth signal which is representative of the concentration of acetylene in said first feed stream at said time $t_2$;

means for establishing a second feed forward control signal in response to said fifth and sixth signals, wherein said second feed forward control signal is a function of the change in the concentration of acetylene in said first feed stream between said time $t_1$ and said time $t_2$ and wherein said second feed forward control signal is scaled so as to be representative of a change in the temperature of said first feed stream and said second feed stream required to maintain the actual concentration of acetylene in said second product stream substantially equal to the desired concentration of acetylene in said second product stream when the concentration of acetylene in said first feed stream changes between said time $t_1$ and said time $t_2$;

means for establishing a seventh signal representative of the flow rate of said first feed stream at said time $t_1$;

means for establishing an eighth signal representative of the flow rate of said first feed stream at said time $t_2$;

means for establishing a third feed forward control signal in response to said seventh and eighth signals, wherein said third feed forward control signal is a function of the change in the flow rate of said first feed stream between said time $t_1$ and said time $t_2$ and wherein said third feed forward control signal is scaled so as to be representative of a change in the temperature of said first feed stream and said second feed stream required to maintain the concentration of acetylene in said second product stream substantially equal to the desired concentration of acetylene in said second product stream when the flow rate of said first feed stream changes between said time $t_1$ and said time $t_2$; and means for summing said second feed forward control signal and said third feed forward control signal with said first feed forward control signal and said feed back control signal to establish said temperature control signal.

3. Apparatus in accordance with claim 2 wherein said first feed forward control signal is characterized by $$FF1 = (K2 - CO_2)(K1)((CO_2 - CO_1)/(t_2 - t_1)) \quad (1)$$

where $FF1$ = the magnitude of said first feed forward control signal;

$CO_1$ = the concentration of carbon monoxide in said first feed stream at said time $t_1$;

$CO_2$ = the concentration of carbon monoxide in said first feed stream at said time $t_2$; and $K1$ and $K2$ = constants, wherein said second feed forward control signal is characterized by $$FF2 = ((AC_2 - AC_1)/(t_2 - t_1))(K4) \quad (2)$$

where $FF2$ = the magnitude of said second feed forward control signal;

$AC_1$ = concentration of acetylene in said first feed stream at said time $t_1$;

$AC_2$ = concentration of acetylene in said first feed stream at said time $t_2$; and $K4$ = a constant, and wherein said third feed forward control signal is characterized by $$FF3 = ((F_2 - F_1)/t_2 - t_1))(K3) \quad (3)$$

where $FF3$ = the magnitude of said third feed forward control signal;

$F_1$ = flow rate of said first feed stream at said time $t_1$;

$F_2$ = flow rate of said first feed stream at said time $t_2$; and $K3$ = a constant.

4. Apparatus in accordance with claim 1 wherein said means for manipulating the temperature of said first feed stream and the temperature of said second feed stream in response to said temperature control signal comprises:

a first heat exchanger means operably located in said means for supplying said first feed stream;

means for supplying a heating fluid to said first heat exchanger means;

bypass conduit means for bypassing at least a portion of said first feed stream around said first heat exchanger means;

means for establishing a fifth signal representative of the temperature of said first feed stream;

first temperature controller means;

means for providing said temperature control signal and said fifth signal to said first temperature controller means, wherein said first temperature controller means establishes a sixth signal which is representative of the desired temperature of said first feed stream at said time $t_2$ in response to said temperature control signal and wherein said first temperature controller means compares said fifth signal and said sixth signal and establishes a seventh signal which is responsive to the difference between said fifth signal and said sixth signal;

means for manipulating the flow rate of said first feed stream through said bypass conduit means in response to said seventh signal to thereby manipulate the temperature of said first feed stream supplied to said first catalyst bed;

a second heat exchanger means operably located in said means for supplying said second feed stream;

means for supplying a cooling fluid to said second heat exchanger means;

bypass conduit means for bypassing a portion of said second feed stream around said second heat exchanger means;

means for establishing an eighth signal representative of the temperature of said second feed stream;

second temperature controller means;

means for providing said temperature control signal and said eighth signal to said second temperature controller means, wherein said second temperature controller means establishes a ninth signal representative of the desired temperature of said second feed stream at said time $t_2$ in response to said temperature control signal and wherein said temperature controller means compares said eighth signal and said ninth signal and establishes a tenth signal which is responsive to the difference between said eighth signal and said ninth signal; and means for manipulating the flow rate of said second feed stream through said bypass conduit means in response to said tenth signal to thereby manipulate the temperature of said second feed stream supplied to said second catalyst bed.

5. A method for controlling a selective hydrogenation process wherein acetylene is removed from an olefin-rich first feed stream which contains acetylene and carbon monoxide and wherein said first feed stream is supplied to the first of two reaction zones in series, said method comprising the steps of:

establishing a first signal representative of the concentration of carbon monoxide in said first feed stream at a time $t_1$;

establishing a second signal representative of the concentration of carbon monoxide in said first feed stream at a time $t_2$ which is later in time than said time $t_1$;

establishing a first feed forward control signal in response to said first and second signals, wherein said first feed forward control signal is a function of the concentration of carbon monoxide in said first feed stream at said time $t_2$ and a function of the change in the concentration of carbon monoxide in said first feed stream between said time $t_1$ and said time $t_2$ and wherein said first feed forward control signal is scaled so as to be representative of a change in the temperature of said first feed stream and the product stream from said first reaction zone, which is provided as a second feed stream to said second reaction zone, required to maintain the actual acetylene concentration in a second product stream from said second reaction zone substantially equal to a desired acetylene concentration in said second product stream when the concentration of carbon monoxide changes between said time $t_1$ and said time $t_2$;

establishing a third signal representative of the actual acetylene concentration in said second product stream at said time $t_2$;

establishing a fourth signal representative of the desired acetylene concentration in said second product stream;

comparing said third signal and said fourth signal and establishing a feed back control signal which is responsive to the difference between said third signal and said fourth signal, wherein said feed back control signal is scaled so as to be representative of a temperature change required to maintain said third signal substantially equal to said fourth signal;

summing said first feed forward control signal and said feed back control signal to establish a temperature control signal; and manipulating the temperature of said first feed stream and the temperature of said second feed stream in response to said temperature control signal.

6. A method in accordance with claim 5 additionally comprising the steps of:

establishing a fifth signal which is representative of the concentration of acetylene in said first feed stream at said time $t_1$;

establishing a sixth signal which is representative of the concentration of acetylene in said first feed stream at said time $t_2$;

establishing a second feed forward control signal in response to said fifth and sixth signals, wherein said second feed forward control signal is a function of the change in the concentration of acetylene in said first feed stream between said time $t_1$ and said time $t_2$ and wherein said second feed forward control signal is scaled so as to be representative of a change in the temperature of said first feed stream and said second feed stream required to maintain the actual concentration of acetylene in said second product stream substantially equal to the desired concentration of acetylene in said second product stream when the concentration of acetylene in said first feed stream changes between said time $t_1$ and said time $t_2$;

establishing a seventh signal representative of the flow rate of said first feed stream at said time $t_1$;

establishing an eighth signal representative of the flow rate of said first feed stream at said time $t_2$;

establishing a third feed forward control signal in response to said seventh and eighth signals, wherein said third feed forward control signal is a function of the change in the flow rate of said first feed stream between said time $t_1$ and said time $t_2$ and wherein said third feed forward control signal is scaled so as to be representative of a change in the temperature of said first feed stream and said second feed stream required to maintain the concentration of acetylene in said second product stream substantially equal to the desired concentration of acetylene in said second product stream when the flow rate of said first feed stream changes between said time $t_1$ and said time $t_2$; and summing said second feed forward control signal and said third feed forward control signal with said first feed forward control signal and said feed back control signal to establish said temperature control signal.

7. A method in accordance with claim 6 wherein said first feed forward control signal is characterized by $$FF1 = (K2 - CO_2)(K1)((CO_2 - CO_1)/(t_2 - t_1)) \tag{1}$$

where
 FF1 = the magnitude of said first feed forward control signal;
 $CO_1$ = the concentration of carbon monoxide in said first feed stream at said time $t_1$;
 $CO_2$ = the concentration of carbon monoxide in said first feed stream at said time $t_2$; and
 K1 and K2 = constants, wherein said second feed forward control signal is characterized by $$FF2 = ((AC_2 - AC_1)/(t_2 - t_1))(K4) \tag{2}$$

where

FF2 = the magnitude of said second feed forward control signal;

$AC_1$ = concentration of acetylene in said first feed stream at said time $t_1$;

$AC_2$ = concentration of acetylene in said first feed stream at said time $t_2$; and K4 = a constant, and wherein said third feed forward control signal is characterized by $$FF3 = ((F_2 - F_1)/t_2 - t_1))(K3) \qquad (3)$$

where

FF3 = the magnitude of said third feed forward control signal;

$F_1$ = flow rate of said first feed stream at said time $t_1$;

$F_2$ = flow rate of said first feed stream at said time $t_2$; and

K3 = a constant.

8. A method in accordance with claim 5 wherein said step of manipulating the temperature of said first feed stream and the temperature of said second feed stream in response to said temperature control signal comprises:

providing said temperature control signal and said fifth signal to a first temperature controller means, wherein said first temperature controller means establishes a sixth signal which is representative of the desired temperature of said first feed stream at said time $t_2$ in response to said temperature control signal and wherein said first temperature controller means compares said fifth signal and said sixth signal and establishes a seventh signal which is responsive to the difference between said fifth signal and said sixth signal;

manipulating the bypassing of said first feed stream around a first heat heat exchange means in response to said seventh signal to thereby manipulate the temperature of said first feed stream supplied to said first reaction zone;

establishing an eighth signal representative of the temperature of said second feed stream;

providing said temperature control signal and said eighth signal to a second temperature controller means, wherein said second temperature controller means establishes a ninth signal representative of the desired temperature of said second feed stream at said time $t_2$ in response to said temperature control signal and wherein said temperature controller means compares said eighth signal and said ninth signal and establishes a tenth signal which is responsive to the difference between said eighth signal and said ninth signal; and manipulating the bypassing of said second feed stream around a second heat exchange means in response to said tenth signal to thereby manipulate the temperature of said second feed stream supplied to said second reaction zone.

* * * * *